United States Patent
Boger

(10) Patent No.: US 6,310,209 B1
(45) Date of Patent: Oct. 30, 2001

(54) SYNTHESIS OF CC-1065/DUOCARMYCIN ANALOGS

(75) Inventor: Dale L. Boger, La Jolla, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 09/581,049

(22) PCT Filed: Dec. 8, 1998

(86) PCT No.: PCT/US99/25992

§ 371 Date: Jul. 10, 2000

§ 102(e) Date: Jul. 10, 2000

(87) PCT Pub. No.: WO99/29642

PCT Pub. Date: Jun. 17, 1999

Related U.S. Application Data

(60) Provisional application No. 60/067,960, filed on Dec. 8, 1997.

(51) Int. Cl.$^7$ .................. C07D 215/48; C07D 471/06
(52) U.S. Cl. ........................... 546/69; 546/84; 546/170
(58) Field of Search ........................ 546/69, 84, 170

(56) References Cited

U.S. PATENT DOCUMENTS

| | | | |
|---|---|---|---|
| 5,006,659 | * 4/1991 | Hagen et al. | 546/170 |
| 5,585,499 | 12/1996 | Chari et al. | |
| 5,605,896 | 2/1997 | Leonardi et al. | |
| 5,629,430 | 5/1997 | Terashima et al. | |
| 5,641,780 | 6/1997 | Amishiro et al. | |

OTHER PUBLICATIONS

Chidester, et al., "The Structure of CC-1065, a Potent Antitumor Agent, and Its Binding to DNA", *J. Am. Chem. Soc. 103*: 7629–7635 (1981).

Ichimura, et al., "Duocarmycin A, A New Antitumor Antibiotic From Streptomyces", *J. Antibiot. 41*: 1915–1917 (1996).

Warpehoski, et al., "Acid–Dependent Electrophilicity of Cyclopropylpyrroloindoles. Nature's Masking Strategy for a Potent DNA Alkylator", *J. Am. Chem. Soc. 116*: 7573–7580 (1994).

Boger, et al., "An Efficient Synthesis of 1,2,9,9a–Tetrahydrocyclopropa[c]benz[e]indol–4–one (CBI): An Enhanced and Simplified Analog of the CC–1065 and Duocarmycin Alkylation Subunits", *J. Org. Chem. 60*: 1271–1275 (1995).

Warpehoski, et al., "Enzyme–like Rate Acceleration in the DNA Minor Groove. Cyclopropylpyrroloindole as Mechanism–Based Inactivators of DNA", *J. Am. Chem. Soc. 117*: 2951–2952 (1995).

Boger, et al., "Synthesis, Chemical Properties, and Preliminary Evaluation of Substituted CBI Analogs of CC–1065 and the Duocarmycins Incorporating the 7–Cyano–1,2,9, 9a–tetrahydrocyclopropa[c]benz[e]indol–4–one Alkylation Subunit: Hammett Quantification of the Magnitude of Electronic Effects on Functional Reactivity", *J. Org. Chem. 61*: 4894–4912 (1996).

Boger, et al., "CC–1065 and the Duocarmycins: Understanding their Biological Function through Mechanistic Studies", *Angew. Chem. Int. Ed. Engl. 35*: 1438–1474 (1996).

Boger, et al., "Catalysis of the CC–1065 and Duocarmycin DNA Alkylation Reaction: DNA Binding Induced Conformational Change in the Agent Results in Activation", *Bioorg. Med. Chem. 5*: 263–276 (1997).

Boger, et al., "Duocarmycin SA Shortened, Simplified, and Extended Agents: A Systematic Examination of the Role of the DNA Binding Subunit", *J. Am. Chem. Soc. 119*: 4977–4986 (1997).

Boger, et al., "Reversed and Sandwiched Analogs of Duocarmuycin SA: Establishment of the Origin of the Sequence–Selective Alkylation of DNA and New Insights into the Source of Catalysis", *J. Am. Chem. Soc. 119*: 4987–4998 (1997).

Boger, et al., "CC–1065 and the Duocarmycins: Synthetic Studies", *Chem. Rev. 97*: 787–828 (1997).

Patel, et al., "Total Synthesis of Seco (+) – and ent–(–)– Oxaduocarmuycin SA: Construction of the (Chloromethyl)indoline Alkylating Subunit by a Novel Intramolecular Aryl Radical Cyclization onto a Vinyl Chloride", *J. Org. Chem. 62*: 8868–8874 (1997).

\* cited by examiner

*Primary Examiner*—Floyd D. Higel
*Assistant Examiner*—Sonya N Wright
(74) *Attorney, Agent, or Firm*—Donald G. Lewis

(57) ABSTRACT

The present invention relates to a method for the synthesis of the dihydroindole C-ring found in CC-1065/duocarmycin analogs.

3 Claims, 3 Drawing Sheets

SYNTHESIS OF CC-1065/DUOCARMYCIN ANALOGS

This application is a 371 of PCT/US99/25992 Filed Dec. 8, 1998 which claims benefit of provisional application No. 60/067,960 Filed Dec. 8, 1997.

TECHNICAL FIELD

The present invention relates to a method for the synthesis of the dihydroindole C-ring found in CC-1065/duocarmycin analogs. More particularly, the invention comprises the 5-exo-trig radical cyclization of an aryl halide onto a tethered vinyl chloride forming the dihydroindole C-ring with chlorine installed as a suitable leaving group for subsequent cyclopropane spirocyclization. The versatility of this approach is examined in the context of six CC-1065/duocarmycin analogs previously synthesized in this laboratory.

BACKGROUND

CC-1065 (1; Chidester et al. *J. Am. Chem. Soc.* 1981, 1–3, 7629) and the duocarmycins 2 (Ichimura et al. *J. Antibiot.* 1990, 43, 1037) and 3 (Takahashi et al. *J. Antibiot.* 1988, 41, 1915; Yasuzawa et al. *Chem. Pharm. Bull.* 1995, 43, 378) are the parent members of a potent class of antitumor antibiotics that derive their biological properties through reversible, sequence selective alkylation of DNA (For a review of mechanistic aspects see: Boger, et al. *Angew. Chem., Int. Ed. Engl.* 1996, 35, 230).

Since their disclosure, synthetic efforts have focused on the natural products as well as a great number of rationally designed analogs (For a review of synthetic efforts see: Boger et al. *Chem. Rev.,* 1997, 97, 787). These analogs have served define the fundamental principles underlying the relationships between structure, chemical reactivity and biological properties within this family, and have advanced the understanding of the origin of sequence selectivity and the catalysis of the DNA alkylation reaction by 1–3 (Boger et al. *J. Am. Chem. Soc.* 1997, 119, 4977; Boger et al. *J. Am. Chem. Soc.* 1997, 119, 4987; Boger et al. *Biorg. Med. Chem.* 1997, 5, 263; Warpehoski et al. *J. Am. Chem. Soc.* 1994, 116, 7573; Warpehoski et al. *J. Am. Chem. Soc.* 1995, 117, 2951).

Common synthetic routes to many of the duocarmycin and CC-1065 analogs incorporate the same transformation via a four step procedure highlighted by an in-situ trap of a primary radical with TEMPO (TEMPO=2,2,6,6-tetramethyl-1-piperidinyloxy free radical) followed by its reductive removal and conversion to the chloride as depicted for the synthesis of CBI (Boger et al. *J. Org. Chem.* 1995, 60, 1271) as illustrated in FIG. 4.

It would be beneficial to have a more direct and higher yielding transformation to obtain the dihydroindole C-ring found in CC-1065/duocarmycin analogs. What is needed, therefore, is an efficient and general method for the synthesis of the dihydroindole C-ring found in CC-1065/duocarmycin analogs with less steps than the standard four step TEMPO procedure as described above.

SUMMARY OF THE INVENTION

One aspect of the invention is directed to a 2 step synthesis of the dihydroindole C-ring found in CC-1065/duocarmycin analog. An aryl halide is alkylated with 1,3-dichloropropene and a catalytic amount of n-tetrabutylammonium iodide for forming a vinyl chloride. The vinyl chloride is then cyclized under conditions using tribuytyl tin hydride, catalytic AIBN and toluene as the solvent for forming the dihydroindole C-ring of the CC-1065/duocarmycin analog.

Another aspect of the invention is directed to the following compounds:

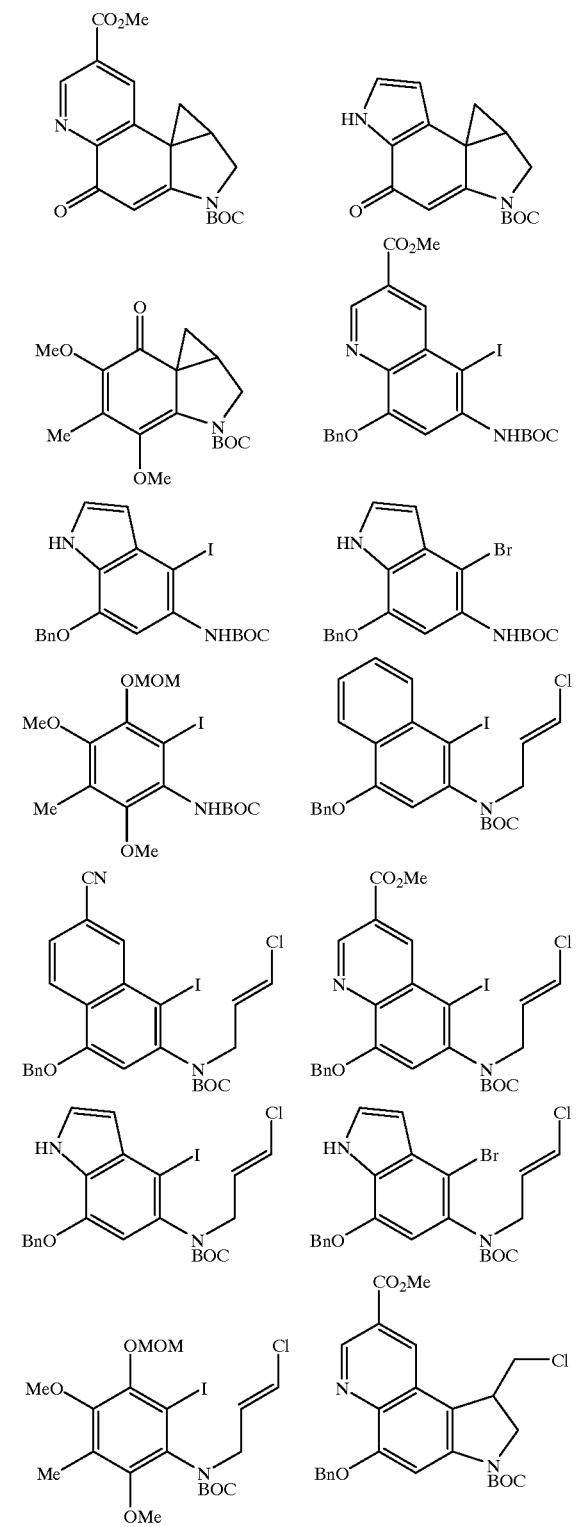

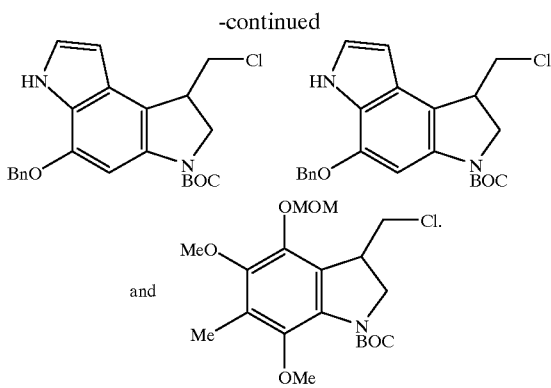

DETAILED DESCRIPTION OF THE INVENTION

Figure 4:
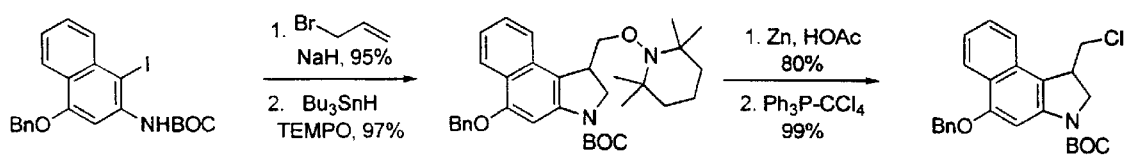
FIG. 4 shows the standard four step procedure highlighted by an in-situ trap of a primary radical with TEMPO (TEMPO=2,2,6,6-tetramethyl-1-piperidinyloxy free radical) followed by its reductive removal and conversion to the chloride as depicted for the synthesis of CBI.
Figure 5:
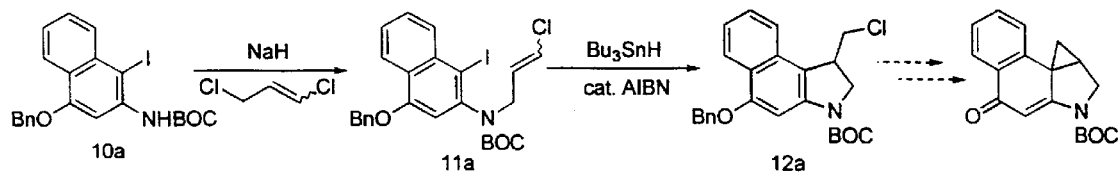
FIG. 5 illustrates the transformation from compound 10a to 12a and the subsequent formation of a cyclopropyl ring.

The invention is directed to a two-step transformation directed to the synthesis of 6 CC-1065/duocarmycin analogs using a novel intramolecular aryl radical cyclization onto a vinyl chloride to form the dihydroindole C-ring found in 6 CC-1065/duocarmycin analogs. This transformation represents a potential two-step improvement to the synthetic route to many other analogs, which most recently incorporated the same transformation via a four step procedure highlighted by an in-situ trap of a primary radical with TEMPO (TEMPO=2,2,6,6-tetramethyl-1-piperidinyloxy free radical) followed by its reductive removal and conversion to the chloride as depicted for the synthesis of CBI (Boger et al. *J. Org. Chem.* 1995, 60, 1271) as illustrated in FIG. 4.

Figure 3:
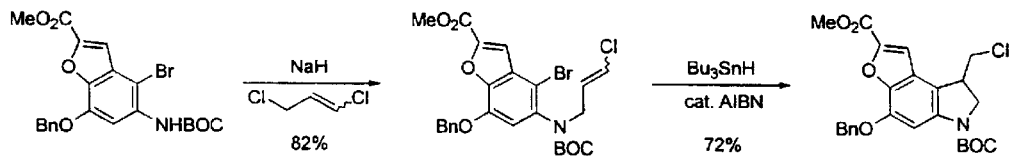
FIG. 3 shows the novel intramolecular aryl radical cyclization onto a tethered vinyl chloride to install the dihydroindole C ring with chlorine installed as a suitable leaving group for subsequent cyclopropane spirocyclization.

Patel et al. describes the synthesis of an analog named Oxa-duocarmycin SA which utilizes a novel intramolecular aryl radical cyclization onto a tethered vinyl chloride to install the dihydroindole C ring with chlorine installed as a suitable leaving group for subsequent cyclopropane spirocyclization as described in FIG. 3.

Application of this improved two-step transformation to the synthetic routes reported for a number of the analogs synthesized in this laboratory would serve to establish the versatility of this approach to the synthesis of CC-1065 and duocarmycin analogs.

Figure 6:
FIG. 6 shows a table which illustrates the results of the two-step synthesis of 3-chloro-methylindolines with the following conditions: a NaH, 1,3-dichloropropene, DMF, 25° C.; b NaH, 1,3-dichloropropene, nBu$_4$NI, DMF, 25° C.; c AIBN (cat.), Bu$_3$SnH, benzene, 60–75° C.; d AIBN (cat.), Bu$_3$SnH, toluene, 90° C. wherein each compound uses the same transformation as shown in FIG. 6.

With this goal in mind, the C-ring construction for CBI (4; Boger et al. *J. Org. Chem.* 1995, 60, 1271, CCBI (5; Boger et al. *J. Org. Chem.* 1996, 61, 4894), CPyI (6), desmethyl-CPI (7), iso-CBI (8), and the mitomycin-hybrid (9) was investigated. The appropriately functionalized aryl halides (10a–g), which were obtained either through direct electrophilic halogenation (entries 1–5) or directed ortho metallation (entries 6 and 7) and halide quench, were alkylated with 1,3 dichloropropene to complete the radical cyclization precursors (11a–g) in high yields. Treatment with BU$_3$SnH and a catalytic amount of AIBN (AIBN=2,2'-azobisisobutyronitrile) with heating in benzene or toluene very cleanly effected 5-exo-trig radical cyclization to form the 3-chloromethyl indoline C-ring present in each of the analogs (12a–g) as illustrated in FIG. 6.

This two-step transformation works well with benzene, naphthalene, indole and quinoline derivatives, aryl iodides as well as aryl bromides, with little to no deterioration in the consistently high yields for both steps. Brief optimization efforts revealed that higher yields may sometimes be obtained with addition of n-Bu$_4$NI to the alkylation reaction, as well as substitution of toluene and higher reaction temperature for benzene. It was observed, as also noted by Patel et al. that deoxygenation of the solvent prior to radical cyclization may enhance both the rate and yield of the reaction.

In summary, this novel intramolecular aryl radical cyclization onto a vinyl chloride, as introduced by Patel, was successfully applied to the C-ring synthesis of 6 CC-1065/duocarmycin analogs. This application has effectively shortened the synthesis of each of these analogs by two steps. Clearly the versatility of this approach, combined with the high conversions for both steps, assure its use in future rational analog design in the CC-1065/duocarmycin family of antitumor antibiotics.

While a preferred form of the invention has been shown in the drawings and described, since variations in the preferred form will be apparent to those skilled in the art, the invention should not be construed as limited to the specific form shown and described, but instead is as set forth in the following claims.

Experimental Protocals

General $^1$H and $^{13}$C nmr spectra were recorded either on a Bruker AM-250, a Bruker AMX-400 or a Bruker AMX-500 spectrometer. Residual protic solvent CHCl$_3$ ($\delta_H$=7.26 ppm, $\delta_c$=77.0), d$_4$-methanol ($\delta_H$=3.30 ppm, $\delta_c$=49.0) and D$_2$O ($\delta_H$=4.80 ppm, $\delta_c$ (of CH$_3$CN)=1.7 ppm) or TMS ($\delta_H$=0.00 ppm) were used as internal reference. Coupling constants were measured in Hertz (Hz). HRMS were recorded using FAB method in a m-nitrobenzylalcohol (NBA) matrix doped with NaI or CsI. Infrared spectra were recorded on a Perkin-Elmer FTIR 1620 spectrometer. Enantiomeric excess was determined by HPLC using a Daicel Chemical Industries CHIRALPAK AD column. Optical rotations were measured with an Optical Activity AA-1000 polarimeter. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel F$_{254}$) and visualized by cerium molybdophosphate or ninhydrin. Diethyl ether, tetrahydrofuran (THF) and toluene (PhCH₃) were distilled from sodium-benzophenone ketyl, dichloromethane (DCM) and acetonitrile from calcium hydride. Other solvents and reagents were purified by standard procedures if necessary.

General Experimental Procedure for Individual Synthesis of 12a–g as Shown in FIG. 6

A solution of the aryl iodide (one of 10a–g as shown in FIG. 6 obtained from the sources or conditions as described herein; aryl iodide is obtained from the following sources:) in anhydrous DMF (0.1M) at 0° C. was treated with NaH (2.0 equiv.) in small portions. The resulting suspension was stirred 15 min and treated with neat 1,3-dichloropropene (5.0 equiv) in a slow dropwise manner, followed by catalytic Bu₄NI (0.1 equiv.; n-tetrabutylammonium iodide ). The reaction mixture was warmed to 25° C. and stirred for 12 h. The reaction mixture was quenched with the addition of 5% aqueous NaHCO₃, and the aqueous layer was extracted with EtOAc. The combined organic extracts were washed with H₂O, dried (Na₂SO₄) and concentrated under reduced pressure. The crude was purified by flash column chromatography. A solution of one of 11a–g in anhydrous benzene (0.1M; alternatively substitution of toluene and higher reaction temperature can optimize yield, due to higher temperatures) was treated with Bu₃SnH (1.05 equiv.) and catalytic AIBN (0.1 equiv.) and deoxygenated with a stream of dry N₂ gas. The solution was heated to 80° C. for 2 h and concentrated in vacuo. The crude was purified by flash column chromatography to form one of compounds 12a–g.

Synthesis of Cyclopropane via Spirocyclization

Figure 1:
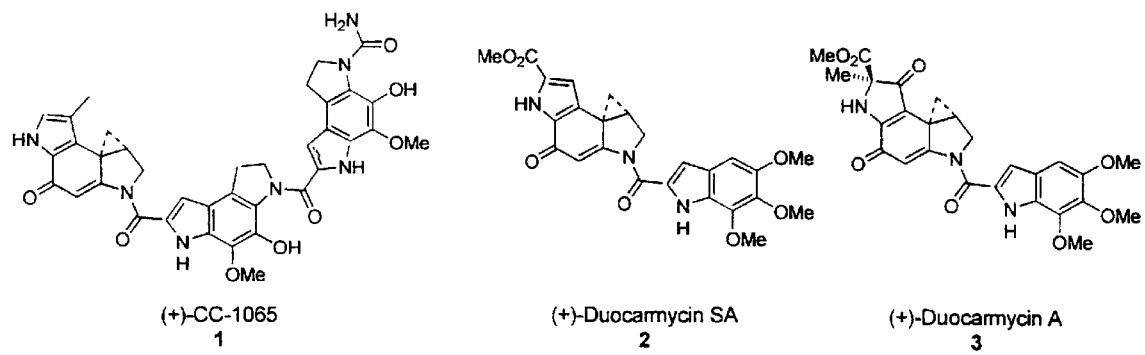
FIG. 1 shows CC-1065 (1) and the duocarmycins (2) and (3). The compounds are parent members of a potent class of antitumor antibiotics.
Figure 2:
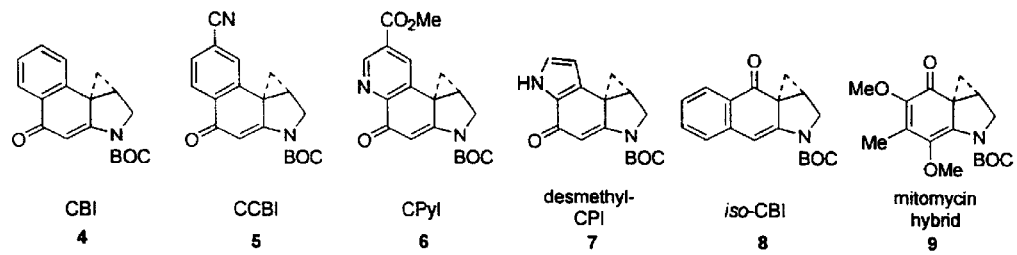
FIG. 2 shows CBI (4) (5), CPyI (6), desmethyl-CPI (7), iso-CBI (8), and the mitomycin-hybrid (9) which are compounds of interest in this application.

The chlorine group of the dihydroindole C-ring is installed as a suitable leaving group for cyclopropane spirocyclization. Methodologies for subsequent spirocyclization and further aklyation of the resultant cyclopropane C-ring system to the DNA portion of CC-1065 and the duocarmycins is well known in the art. A representative spirocyclization is accomplished via treatment of 12(a–g) with NaH (3 equiv, THF, 0° C., 30 min) to provide (4–9; as shown in FIG. 2). Similarly, acid-catalyzed deprotection of 12(a–g) (3N HCl-EtOAc, 25° C., 20 min) followed by spirocyclization of the crude indoline hydrochloride salt upon exposure to 5% aqueous NaHCO₃-THF (1:1, 25° C., 1.5 h, 93%) can also provide (4–9; as shown in FIG. 2).

Synthesis of Compounds 4–9 as Shown in FIG. 2

A solution of 12(a–g; one of the compounds in FIG. 6; obtained from the sources or conditions as described herein) (1.5 mg, 4.1 μmol) in tetrahydrofuran-dimethylformamide (3:1, 200 μL) at 0° C. under N₂ was treated with suspension of NaH (0.5 mg, 60% in an oil dispersion, 12 μmol, 3 equiv). The reaction mixture was allowed to stir at 0° C. and for 30 min before the addition of pH 7 phosphate buffer (0.2 M, 250 μL) and 2 mL of tetrahydrofuran. The organic layer was dried (Na₂SO₄) and concentrated in vacuo. Chromatography (SiO₂, 20–30% Ethylacetate-hexane gradient elution) afforded (4–9; as shown in FIG. 2): Alternative Spyrocyclization: 12(a–g; one of the compounds) (5 mg, 1.37 μmol) was treated with anhydrous 3N HCl-Ethylacetate (0.4 mL) at 24° C. for 20 min. The solvent was removed in vacuo to afford the crude, unstable amine hydrochloride. This residue was treated with 5% aqueous NaHCO₃ (0.4 mL) and tetrahydrofuran (0.4 mL) at 24° C. under N₂, and the two phase mixture was stirred for 1.5 h (24° C.). The reaction mixture was extracted with Ethylacetate (3×2 mL) and the combined extracts were washed with H₂O (2 mL), dried (Na₂SO₄) and concentrated in vacuo. Chromatography (SiO₂, 10% CH₃OH—CH₂Cl₂) afforded (4–9; as shown in FIG. 2).

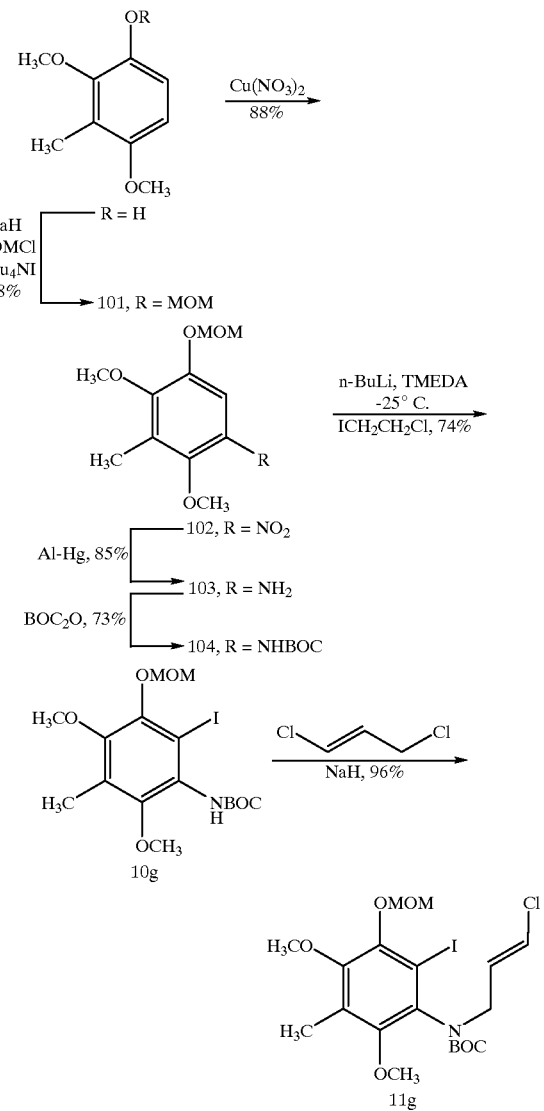

2,4-(Dimethoxy)-3-(methyl)-methoxymethyl phenyl ether (101)

A solution of 2,4-(dimethoxy)-3-methylphenol (1.0 g, 5.95 mmol) in 60 mL of anhydrous DMF at 0° C. was treated with NaH (357 mg, 9.91 mmol) in several portions over 5 min. After 10 min, Bu₄NI (219 mg, 0.60 mmol) was added followed by the dropwise addition of ClCH₂OCH₃ (0.68 mL, 8.91 mmol). The reaction mixture was stirred at 25° C. for 36 h before the reaction was quenched by the slow addition of 30 mL of H₂O. The aqueous layer was extracted with EtOAc (3 (30 mL). The organic layers were combined, washed with 10% aqueous NaHCO₃ (50 mL) and H₂O (4(20 mL), dried (Na₂SO₄), and concentrated under reduced pressure. Flash chromatography (SiO₂, 3 (10 cm, 10% EtOAc/ hexane) provided 101 (1.11 g, 88%) as a light yellow oil: ¹H NMR (CDCl₃, 250 MHz) δ6.92 (d, J=8.8 Hz, 1H), 6.51 (d, J=8.8 Hz, 1H), 5.13 (s, 2H), 3.79 (s, 3H), 3.76 (s, 3H), 3.50 (s, 3H), 2.13 (s, 3H); ¹³C NMR (CDCl₃, 62.5 MHz) δ153.5, 149.2, 144.3, 121.0, 114.4, 105.3, 96.0, 60.4, 56.0, 55.7, 8.9; IR (film) ν_{max} 2937, 2833, 1595, 1487, 1440, 1420 cm⁻¹; FABHRMS (NBA) m/z 212.1040 (C₁₁H₁₆O₄ requires 212.1049).

2,4-(Dimethoxy)-3-(methyl)-5-(nitro)-methoxymethyl phenyl ether (102)

A solution of 101 (1.11 g, 5.21 mmol) in 18 mL freshly distilled $Ac_2O$ at 0° C. was treated with $Cu(NO_3)_2 \cdot 2.5\ H_2O$ (2.41 g, 10.4 mmol) in several portions over 5 min. The reaction mixture was stirred for 2 h at 0° C., then 1 h at 25° C. before the reaction was poured over $H_2O$ (50 mL) and extracted with EtOAc (3 (30 mL). The combined organic layers were washed with saturated aqueous NaCl (50 mL), dried ($Na_2SO_4$), and concentrated under reduced pressure. The crude light yellow oil (1.18 g, 88%) was carried on to the next transformation: $^1H$ NMR ($CDCl_3$, 250 MHz) δ7.54 (s, 1H), 5.18 (s, 2H), 3.87 (s, 3H), 3.81 (s, 3H), 3.48 (s, 3H), 2.21 (s, 3H); $^{13}C$ NMR ($CDCl_3$, 62.5 MHz) δ153.0, 147.8, 145.8, 138.9, 128.2, 110.5, 95.3, 61.8, 60.5, 56.2, 9.5; IR (film) $v_{max}$ 2942, 2829, 1522, 1481, 1344, 1280, 1246 cm$^{-1}$; FABHRMS (NBA) m/z 258.0977 ($C_{11}H_{15}NO_6+H^+$ requires 258.0978).

5-(Amino)-2,4-(dimethoxy)-3-(methyl)-methoxymethyl phenyl ether (103)

A solution of 102 (1.18 g, 4.57 mmol) in 90 mL moist ether (8:2:1 $Et_2O$:EtOH:$H_2O$) was cooled to 0° C., and treated with freshly prepared Al-Hg (1.23 g Al, 45.7 mmol) in small 1 (1 cm pieces. The reaction mixture was stirred vigorously for 0.5 h at 0 (C., then 1 h at 25 (C. The reaction mixture was then filtered through Celite, and the Celite was washed thoroughly with $Et_2O$ (5 (20 mL). The solution was then washed with saturated aqueous NaCl (100 mL), dried ($Na_2SO_4$), and concentrated under reduced pressure to afford 103 (0.88 g, 85%) as a crude brown oil, which was immediately carried on to the next step: $^1H$ NMR ($CDCl_3$, 250 MHz) δ6.42 (s, 1H), 5.11 (s, 2H), 3.70 (s, 3H), 3.66 (s, 3H), 3.56 (m, 2H), 3.47 (s, 3H), 2.16 (s, 3H); $^{13}C$ NMR ($CDCl_3$, 250 MHz) δ147.0, 140.4, 140.3, 135.8, 125.4, 102.0, 95.4, 60.6, 59.4, 56.0, 9.34; IR (film) $v_{max}$ 3446, 3359, 2935, 2826, 1617, 1492, 1358 cm$^{-1}$; ESIMS m/z 228 ($C_{11}H_{17}NO_4+H^+$ requires 228).

[N-(tert-Butyloxycarbonyl)amino]-2,4-(dimethoxy)-5-(methoxymethoxy)-3-methylbenzene (104)

A solution of crude 102 (0.88 g, 3.85 mmol) in 40 mL anhydrous THF was treated with $BOC_2O$ (1.73 g, 7.72 mmol) and the reaction mixture was warmed at reflux (65 (C.) for 18 h. The solvents were removed under reduced pressure, and flash chromatography ($SiO_2$, 3 (10 cm, 10% EtOAc/hexane) provided pure 104 as a yellow oil (0.96 g, 76%): $^1H$ NMR ($CDCl_3$, 250 MHz) δ7.72 (br s, 1H), 6.86 (br s, 1H), 5.18 (s, 2H), 3.75 (s, 3H), 3.67 (s, 3H), 3.51 (s, 3H), 2.19 (s, 3H), 1.50 (s, 9H); $^{13}C$ NMR ($CDCl_3$, 100 MHz) δ152.7, 146.4, 143.6, 141.6, 127.8, 124.8, 105.3, 95.5, 80.4, 60.5, 60.4, 56.4, 28.3, 9.5; IR (film) $v_{max}$ 3437, 3341, 2977, 2935, 1731, 1519, 1454, 1422, 1397 cm$^{-1}$; FABHRMS (NBA/CsI) m/z 460.0723 ($C_{16}H_{25}NO_6+Cs^+$ requires 460.0736).

[N-(tert-Butyloxycarbonyl)amino]-2,4-(dimethoxy)-6-(iodo)-5-(methoxymethoxy)-3-methyl benzene (10 g)

A solution of 104 (0.55 g, 1.67 mmol) in 6.6 mL anhydrous THF was cooled to −25 (C. and treated with TMEDA (0.94 mL, 6.18 mmol) followed by n-BuLi (2.5 mL of a 2.5 M solution in hexane, 6.18 mmol) in a slow dropwise manner. The resulting gold solution stirred for 2 h at −25 (C. The reaction mixture was treated with 1-chloro-2-iodoethane (0.45 mL, 6.18 mmol) and stirred for 15 min at 25 (C. The reaction was diluted with $H_2O$ (50 mL) and extracted with $Et_2O$ (3 (30 mL), and the combined organic extracts were washed with saturated aqueous NaCl, dried ($Na_2SO_4$), and concentrated under reduced pressure. Flash chromatography ($SiO_2$, 2.5 (10 cm, 20% EtOAc/hexane) yielded 11 g (560 mg, 74%) as a colorless oil: $^1H$ NMR ($CDCl_3$, 400 MHz) δ5.99 (br s, 1H), 5.10 (s, 2H), 3.75 (s, 3H), 3.69 (s, 3H), 3.65 (s, 3H), 2.17 (s, 3H), 1.49 (s, 9H); $^{13}C$ NMR ($CDCl_3$, 100 MHz) δ153.6, 151.8, 150.5, 146.9, 129.3, 126.7, 99.1, 95.8, 80.6, 60.5, 60.3, 58.5, 28.3, 9.8; IR (film) $v_{max}$ 3321, 2975, 2936, 1722, 1485, 1455, 1390 cm$^{-1}$; FABHRMS (NBA/CsI) m/z 585.9688 ($C_{16}H_{24}INO_6+Cs^+$ requires 585.9703).

[N-(tert-Butyloxycarbonyl)-N-(3-chloro-2-propen-1-yl)amino]-2,4-(dimethoxy)-6-(iodo)-5-(methoxymethoxy)-3-methylbenzene (11 g).

A solution of 10 g (0.610 g, 1.34 mmol) in 13.4 mL anhydrous DMF was cooled to 0 (C., and treated with NaH (60% dispersion in oil, 121 mg, 4.03 mmol) in small portions. The resulting suspension was stirred for 15 min and treated with neat 1,3-dichloropropene (0.52 mL, 5.5 mmol) in a slow dropwise manner, followed by catalytic n-$Bu_4NI$ (50.0 mg, 0.13 mmol). The reaction mixture was warmed to 25 (C. and stirred for 3 h. The reaction mixture was quenched with the addition of saturated aqueous $NaHCO_3$ (50 mL), and the aqueous layer was extracted with EtOAc (3 (30 mL). The combined organic extracts were washed with $H_2O$ (4 (50 mL), dried ($Na_2SO_4$), and concentrated under reduced pressure. Flash chromatography ($SiO_2$, 3 (10 cm, 0–20% EtOAc/hexane gradient) yielded 11 g (0.681 g, 96%) as a colorless mixture of rotamers: $^1H$ NMR ($CDCl_3$, 400 MHz) 2:1 rotamers δ6.15–6.03 (m, 1H), 6.00–5.90 (m, 1H), 5.11–5.03 (m, 2H), 4.17–3.87 (m, 2H), 3.77 and 3.74 (s, 3H), 3.65 and 3.63 (s, 3H), 3.627 and 3.622 (s, 3H), 2.14 and 2.13 (s, 3H), 1.50 and 1.34 (s, 9H); $^{13}C$ NMR ($CDCl_3$, 100 MHz) rotamers δ153.65 and 153.62, 152.8 and 152.1, 151.0 and 150.7, 147.0 and 146.7, 134.5 and 134.0, 129.5 and 129.0, 127.0 and 126.7, 121.0 and 120.6, 99.0, 97.7 and 97.3, 80.8 and 80.6, 60.5 and 60.4, 60.3 and 60.2, 58.5 and 58.4, 50.4, 48.8, 28.3 and 28.2, 9.9; IR (film) $v_{max}$ 2973, 2936, 1704, 1456, 1366 cm$^{-1}$; FABHRMS (NBA/CsI) m/z 659.9655 ($C_{19}H_{27}ClINO_6+Cs^+$ requires 659.9626).

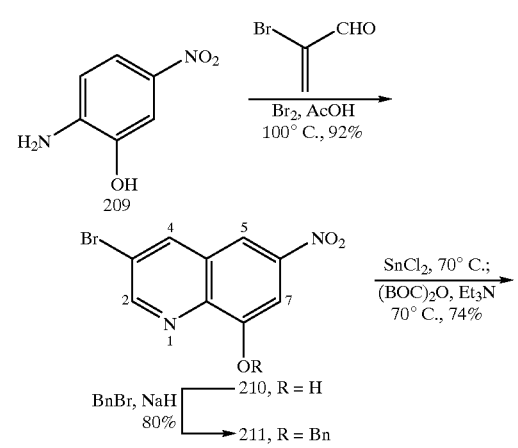

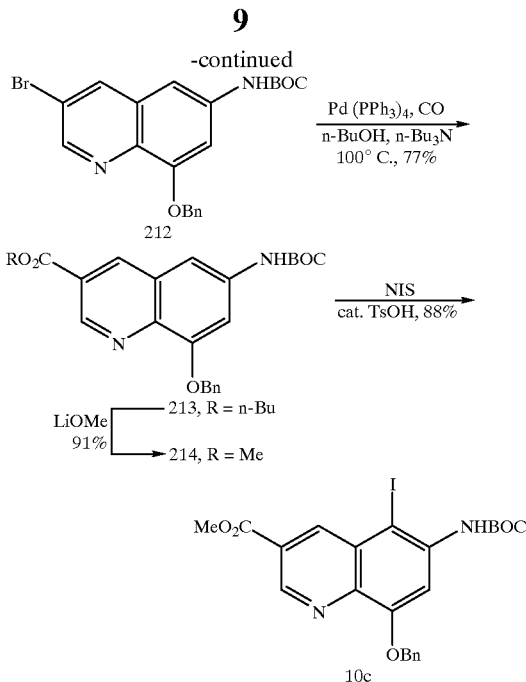

3-Bromo-8-hydroxy-6-nitroquinoline (210)

A solution of 2-bromoacrolein (5 g, 37.0 mmol, 1 equiv) in 110 mL glacial acetic acid at 25° C. was titrated to the appearance of a faint reddish color with bromine (ca. 5.9 g, 37.0 mmol, 1 equiv). 2-Hydroxy-4-nitroaniline (209, 5.7 g, 37.0 mmol, 1 equiv) was added, and the solution was gradually heated to 100 (C. The solution was cooled to 25 (C. after one hour. Filtering and neutralization of the precipitate with 1 M sodium phosphate buffer (pH 7, $Na_2HPO_4$—$NaH_2PO_4$) afforded 9.2 g (9.95 g theoretical, 92%) of 210 as a light yellow solid: mp 240–241 (C; $^1$H NMR (CDCl$_3$, 400 MHz) δ8.93 (d, J=2.0 Hz, 1H), 8.50 (d, J=2.0 Hz, 1H), 8.23 (d, J=2.2 Hz, 1H), 8.18 (s, 1H), 7.92 (s, J=2.3 Hz, 1H); $^{13}$C NMR (DMSO, 62.5 MHz) δ155.1, 152.1, 146.3, 139.5, 139.1, 128.7, 119.1, 113.5, 105.1; IR (film) ($\nu_{max}$ 3408 (br), 3089, 1587, 1553, 1519, 1476, 1389, 1350, 1297, 1263, 1210, 1133, 1079, 929, 931, 839, 804, 734, 633 cm$^{-1}$; ESIMS m/z 269 (M+H$^+$, C$_9$H$_3$BrO requires 269); Anal. Calcd for C$_9$H$_3$BrO: C, 40.18; H, 1.87; N, 10.41. Found: C, 40.21; H, 1.91; N, 9.98.

8-(Benzyloxy)3-bromo-6-nitroquinoline (211)

A solution of 210 (13.7 g, 51 mmol, 1 equiv) in anhydrous DMF (150 mL) was cooled to 4 (C. under nitrogen and treated with KI (1.7 g, 10 mmol, 0.2 equiv) and sodium hydride (60% dispersion in oil, 2.24 g, 56 mmol, 1.1 equiv). Benzyl bromide (7.3 mL, 6.1 mmol, 1.2 equiv) was added after 30 min and the reaction was allowed to warm to 25 (C. After 24 h, the reaction volume was reduced by one-third in vacuo and EtOAc (200 mL) was added. The reaction mixture was poured on H$_2$O (200 mL) and extracted with EtOAc (3 (100 mL). The combined organic extracts were washed with saturated aqueous NaCl (1 (40 ml), dried (Na$_2$SO$_4$) and concentrated. Flash chromatography (SiO$_2$, 5.5 (20 cm, 50–100% CH$_2$Cl$_2$-hexane) afforded 211 (15.63 g, 18.32 g theoretical, 85%) as a yellow solid: mp 170 (C; $^1$H NMR (CDCl$_3$, 400 MHz) δ9.06 (d, J=2.2 Hz, 1H), 8.44 (d, J=2.2 Hz, 1H), 8.25 (d, J=2.2 Hz, 1H), 7.83 (d, J=2.2 Hz, 1H), 7.52 (app d, J=7.4 Hz, 2H), 7.38 (m, 2H), 7.32 (m, 1H), 5.47 (s, 2H); $^{13}$C NMR (CDCl$_3$, 62.5 MHz) δ155.4, 153.3, 146.4, 140.3, 138.8, 135.0, 128.7 (2C), 128.6, 128.4 (2C), 127.5, 119.9, 115.1, 103.3, 71.4; IR (film) ($\nu_{max}$ 3082, 3055, 2933, 2871, 1609, 1567, 1519, 1476, 1450, 1375, 1338, 1311, 1252, 1135, 1093, 976, 912, 842, 741 cm$^{-1}$; FABHRMS (NBA/NaI) m/z 359.0040 (M+H$^+$, C$_{16}$H$_{11}$BrN$_2$O$_3$ requires 359.0031). Anal. Calcd for C$_{16}$H$_{11}$BrN$_2$O$_3$: C, 53.50; H, 3.09; N, 7.80. Found: C, 53.81; H, 3.23; N, 7.48.

3-(Benzyloxy)-3-bromo-6-N-(tert-butyloxycarbonyl) aminoquinoline (212)

A solution of 211 (200 mg, 0.56 mmol, 1 equiv) in EtOAc (1.1 mL) at 25 (C. was treated with SnCl$_2$—2H$_2$O (628 mg, 2.78 mmol, 5 equiv). The reaction mixture was heated to 70 (C. under nitrogen until an orange slurry formed (ca. 0.5 h). After cooling to 25 (C., the reaction mixture was poured on ice and made basic with 1N NaOH. The aqueous layer was filtered and extracted with EtOAc (3 (15 mL). The combined organic layers were treated with saturated aqueous NaCl (1 (10 mL), dried (Na$_2$SO$_4$) and concentrated. The yellow solid was placed under vacuum for 0.5 h and then dissolved in anhydrous dioxane (5 mL) and treated with di-tert-butyl dicarbonate (490 mg, 2.25 mmol, 4.0 equiv) and triethylamine (156 μL, 1.12 mmol, 2.0 equiv). The reaction mixture was warmed to 70° C. under argon for one day. After cooling, the solvent was removed in vacuo. Chromatography (SiO$_2$, 3 (13 cm, 25% EtOAc-hexane) afforded 212 (179 mg, 240 mg theoretical, 74%) as a light yellow solid: mp 162 (C; $^1$H NMR (CDCl$_3$, 500 MHz) δ8.77 (d, J=2.0 Hz, 1H), 8.13 (d, J=2.5 Hz, 1H), 7.47 (app d, J=7.5 Hz, 2H), 7.42 (d, J=2.0 Hz, 1H), 7.35 (m, 2H), 7.28 (m, 1H), 7.01 (d, J=2.0 Hz, 1H), 6.61 (s, 1H), 5.37 (s, 2H), 1.51 (s, 9H); $^{13}$C NMR (CDCl$_3$, 125 MHz) δ154.9, 152.4, 148.3, 137.9, 136.3, 136.2, 135.4, 131.0, 128.6 (2C), 128.0, 127.3 (2C), 118.6, 104.7, 103.6, 81.1, 70.9, 28.3 (3C); IR (film) ($\nu_{max}$ 3354, 2971, 2919, 1807, 1766, 1724, 1621, 1450, 1367, 1310, 1253, 1217, 1160, 1123, 1061, 843, 771, 699, 657 cm$^{-1}$; FABHRMS (NBA/CsI) m/z 429.0825 (M+H$^+$, C$_{21}$H$_{21}$BrN$_2$O$_3$ requires 429.0814).

n-Butyl8-(benzyloxy)-6-N-(tert-butyloxycarbonyl) aminoquinoline-3-carboxylate (213)

A solution of 212 (4.4 g, 10.1 mmol, 1 equiv) in 85 mL n-BuOH was cooled to –78 (C. and degassed under vacuum. Pd(PPh$_3$)$_4$ (1.2 g, 1.0 mmol, 0.1 equiv) and n-BU$_3$N (2.9 mL, 12.1 mmol, 1.2 equiv) were added and the solution was purged with nitrogen. The reaction mixture was then flushed with carbon monoxide and then slowly heated to 100 (C. under a CO atmosphere. Upon complete reaction (ca. 12 h), 50 mL H$_2$O and 50 mL saturated aqueous NH$_4$Cl were added. The organic layer was separated and the aqueous layer was extracted with EtOAc (3 (50 mL). The combined organic layers were washed with saturated aqueous NaCl (1 (40 mL), dried (Na$_2$SO$_4$) and concentrated. Chromatography (SiO$_2$, 5.5 (20 cm, 25% EtOAc-hexane) afforded 213 (3.55 g, 4.55 g theoretical, 78%) as a yellow solid: mp 135–136 (C; $^1$H NMR (CDCl$_3$, 400 MHz) δ9.31 (d, J=2.0 Hz, 1H), 8.66 (d, J=2.1 Hz, 1H), 7.61 (d, J=1.8 Hz, 1H), 7.49 (app d, J=7.4 Hz, 2H), 7.35 (app t, J=7.2 Hz, 2H), 7.29 (m, 1H), 7.11 (d, J=2.1 Hz, 1H), 6.64 (br s, 1H), 5.39 (s, 2H), 4.38 (t, J=6.6 Hz, 2H), 1.78 (m, 2H), 1.52 (s, 9H), 1.49 (m, 2H, buried under 1.52 ppm), 0.98 (t, J=7.4 Hz, 3H); $^{13}$C NMR (acetone d$_6$, 100 MHz) δ165.7, 155.7, 153.5, 146.8, 139.8, 139.5, 137.8, 137.7, 129.5, 129.1 (2C), 128.6, 128.4 (2C), 124.8, 107.1, 106.9, 80.4, 71.2, 65.5, 31.3, 28.3 (3C), 19.8, 13.9. IR (film) ($_{max}$ 3222, 3049, 2958, 2930, 2876, 1717, 1617, 1544, 1503, 1430, 1362, 1271, 1239, 1157, 1065 cm$^{-1}$; FABHRMS (NBA/CsI) m/z 451.2249 (M+H$^+$, $C_{26}H_{30}N_2O_5$ requires 451.2233).

Methyl-8-(benzyloxy)-6-N-(tert-butyloxycarbonyl) aminoquinoline-3-carboxylate (214)

A solution of 213 (2.9 g, 6.4 mmol, 1.0 equiv) in 70 mL MeOH was cooled to 4 (C. under nitrogen and treated with LiOMe (275 mg, 7.1 mmol, 1.1 equiv). The reaction mixture was allowed to warm to 25 (C. after 20 min. Upon complete reaction (ca. 1.5 h), 100 mL H$_2$O was added. The organic layer was separated and the aqueous layer was extracted with EtOAc (3 (30 mL). The organic layers were combined, washed with saturated aqueous NaCl (1 (30 mL), dried (Na$_2$SO$_4$) and concentrated. Chromatography (SiO$_2$, 5 (19 cm, 25–30% EtOAc-hexane) afforded 214 (2.39 g, 2.63 g theoretical, 91%) as a yellow solid: mp 173–174 (C; $^1$H NMR (CDCl$_3$, 400 MHz) δ9.29 (d, J=2.0 Hz, 1H), 8.66 (d, J=2.1 Hz, 1H), 7.56 (d, J=1.8 Hz, 1H,), 7.45 (m, 2H), 7.30 (m, 2H), 7.25 (m, 1H), 7.18 (d, J=2.0 Hz, 1H), 6.85 (s, 1H), 5.36 (s, 2H), 3.98 (s, 3H), 1.50 (s, 9H); $^{13}$C NMR (CDCl$_3$, 125 MHz) δ165.9, 154.6, 152.6, 146.9, 138.6, 137.9, 137.8, 136.0, 128.5, 128.4 (2C), 127.9, 127.3 (2C), 123.8, 106.5, 105.5, 80.8, 70.8, 52.4, 28.2 (3C); IR (film) ($_{max}$ 3333, 3241, 2974, 1723, 1621, 1580, 1539, 1497, 1431, 1390, 1364, 1277, 1231, 1164, 1126, 1103, 1062, 1000, 882, 846, 795, 749, 697, 662 cm$^{-1}$; FABHRMS (NBA/CsI) m/z 409.1773 (M+H$^+$, $C_{23}H_{24}N_2O_5$ requires 409.1763).

Methyl 8-(benzyloxy)-6-[N-(tert-butyloxycarbonyl) amino]-5-iodoquinoline-3-carboxylate (10c)

A solution of 214 (2.13 g, 5.2 mmol, 1 equiv) in 85 mL of a 1:1 mixture of THF—CH$_3$OH was cooled to 4 (C. and treated with 40 mg TsOH (or H$_2$SO$_4$) in 0.5 mL THF. N-Iodosuccinimide (1.4 g, 6.2 mmol, 1.2 equiv) in 10 mL THF was then slowly added over 10 min. After 1.5 h, the reaction mixture was warmed to 25 (C. and then stirred 45 h. Upon complete reaction, 100 mL saturated aqueous NaHCO$_3$, 100 mL Et$_2$O, and 100 mL H$_2$O were added. The organic layer was separated and the aqueous layer was extracted with Et$_2$O (3 (50 mL) and EtOAc (1 (50 mL). The organic layers were combined, washed with saturated aqueous NaHCO$_3$ (1 (50 mL) and saturated aqueous NaCl (1 (50 mL), dried (Na$_2$SO$_4$) and concentrated. Chromatography (SiO$_2$, 5 (19 cm, hexanes then 30% EtOAc-hexane) provided 10c (2.34 g, 2.78 g theoretical, 84%, typically 80–88%) as a yellow solid: mp 182–183 (C.; $^1$H NMR (CDCl$_3$, 400 MHz) δ9.27 (d, J=1.9 Hz, 1H), 8.96 (d, J=1.9 Hz, 1H), 8.40 (s, 1H), 7.58 (m, 2H), 7.36 (m, 2H), 7.27 (m, 1H), 7.26 (s, 1H), 5.43 (s, 2H), 4.01 (s, 3H), 1.55 (s, 9H); $^{13}$C NMR (CDCl$_3$, 62.5 MHz) δ165.4, 155.0, 152.3, 147.6, 141.9, 139.8, 139.7, 135.8, 129.6, 128.5 (2C), 128.1, 128.0 (2C), 125.1, 105.6, 81.7, 78.4, 71.1, 52.6, 28.2 (3C); IR (film) ($_{max}$ 3384, 2974, 1723, 1595, 1554, 1498, 1431, 1400, 1359, 1328, 1262, 1226, 1149, 995, 754 cm$^{-1}$; FABHRMS (NBA/CsI) m/z 535.0743 (M+H$^+$, $C_{23}H_{23}IN_2O_5$ requires 535.0730).

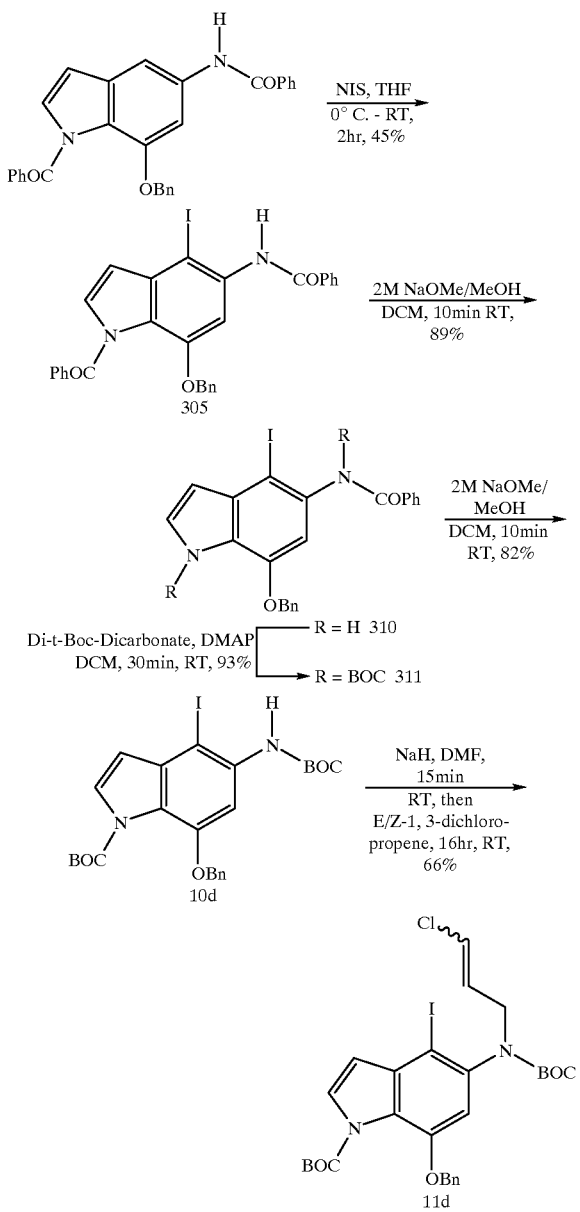

N$^5$,1-Dibenzoyl-5-amino-7-(benzyloxy)-4-iodoindole (305)

The above indole (118 mg, 0.26 mmol) was stirred in THF (1 mL) and toluenesulfonic acid (26 mg, 0.13 mmol) was added. The solution was cooled to 0° C. and N-iodosuccinimide (71 mg, 0.312 mmol) in THF (1 mL) was added. The reaction was allowed to warm to 25° C. over 1 hr. After 16 hr, a further portion of N-iodosuccinimide (15 mg, 0.065 mmol) was added and the reaction was stirred for a further 24 hr. Saturated sodium bicarbonate solution (1 mL) and water (4 mL) were then added and the resulting mixture was extracted with chloroform (3×5 mL). The organic layers were combined, dried (MgSO$_4$) and volatiles were removed under reduced pressure. The residue was purified by flash column chromatography (silica, ethyl acetate/hexane 3:7, 2.5×15 cm) and crystallized from ethyl acetate to give the expected product (305) as a yellow solid (67 mg, 45%); $^1$H NMR δ(ppm) (CDCl$_3$) 8.15 (s, 1H, NH), 7.99 (d, 2H J=Hz), 7.64 (d, 2H, J=Hz), 7.58–7.47 (m, 4H, ArH), 7.30–7.17 (m, 5H, ArH), 6.58 (d, 1H, J=3.6 Hz), 4.92 (s, 2H). 13C NMR δ(ppm) 168, 165.5, 147.3, 136.2, 135.8, 134.9, 134.7, 134.1, 132.2, 132.1, 129.8, 129.6, 129.5, 129.0, 128.4, 128.3, 128.2, 127.8, 127.7, 127.1, 127.0, 122.4, 110.6, 102.1, 71.9, 70.6 IR (neat) $v_{max}$ 3058, 1703, 1678, 1598, 1332, 1279, 1237, 695 cm$^{-1}$ Mass Spectrum (FAB, NAB/CsI) 705 (M$^+$+Cs$^+$).

$N^5$-Benzoyl-5-amino-7-(benzyloxy)-4-iodoindole (310)

The above iodo-compound (305) (193 mg, 0.34 mmol) was stirred in dichloromethane (10 mL). Sodium methoxide in methanol (0.523 mL, 1.04 mmol) was added and the solution was stirred at RT for 10 min. Water (50 mL) and ethyl acetate (50 mL) were added and organic layer was separated, dried (MgSO$_4$) and evaporated to give the crude product. Chromatography (2×15 cm SiO$_2$, ethyl acetate/hexanes 1:3) gave the pure compound (142 mg, 89%), Rf 0.2 (SiO$_2$, ethyl acetate/hexanes 1:3) as a colourless solid: $^1$H NMR (CDCl$_3$, 400 MHz) 8.61 (s, 1H, NH), 8.31(s, 1H, NH), 8.05 (s, 1H), 8.00 (d, 1H, J=6.8 Hz), 7.53 (m, 5H), 7.37 (m, 3H), 7.21 (dd, 1H, J=2.8, 1.4 Hz), 6.43 (dd, 1H, J=2.7, 1.2 Hz), 5.28 (s, 2H); IR (neat) $v_{max}$ 3290, 3010, 1658, 1573, 1535, 1355 cm$^{-1}$; FABHRMS (NBA-CsI) m/z 600.9408. (M+Cs$^+$, C$_{22}$H$_{17}$IN$_2$O$_2$ requires 600.9389).

$N^5$-Benzoyl-$N^5$,1-di-(tert-butoxycarbonyl)-5-amino-7-(benzyloxy)-4-iodoindole (311)

Di-tert-butyl dicarbonate (687 mg, 3.16 mmol) and DMAP (128 mg, 1.04 mmol) were added to a stirred solution of compound 310 (255 mg, 0.54 mmol) in dichloromethane (6 mL). After 30 min at RT the solution was directly subjected to chromatography (2×15 cm SiO$_2$, ethyl acetate/hexane 1:4) to give the pure product (390 mg, 93%) as a colorless oil (Rf 0.80, SiO$_2$, ethyl acetate/hexane 1:3); $^1$H NMR (CDCl$_3$, 400 MHz) 7.81 (d, 2H, J=6.9 Hz), 7.55 (d, 1H, J=3.6 Hz), 7.45 (m, 5H), 7.31 (m, 3H), 6.82 (s, 1H), 6.57 (d, 1H, J=3.6 Hz), 5.15 (s, 2H), 1.47 (s, 9H), 1.22 (s, 9H); FABHRMS (NBA-CsI) m/z 801.0402 (M+Cs$^+$, C$_{32}$H$_{33}$IN$_2$O$_6$ requires 801.0438).

$N^5$,1-Di-(tert-butoxycarbonyl)-5-amino-7-(benzyloxy)-4-iodoindole (10d)

Sodium methoxide in methanol (2M, 0.224 mL, 0.44 mmol) was added to a stirred solution of compound (311) (150 mg, 0.22 mmol) in dichloromethane (5 mL). After 10 min at RT, water (25 mL) and ethyl acetate (25 mL) were added and the organic layer was separated. The aqueous layer was extracted with ethyl acetate (25 mL) and the combined organic layers were dried (MgSO$_4$) and concentrated. Chromatography (2×15 cm SiO$_2$, gradient elution ethyl acetate/hexanes 1:9 to ethyl acetate/hexanes 1:3) gave the pure compound (102 mg, 82%), Rf 0.8 (SiO$_2$, ethyl acetate/hexanes 1:3) as a colourless oil: $^1$H NMR (CDCl$_3$, 400MHz) 7.83 (br s, 1H, NH), 8.00 (d, 1H, J=6.8 Hz), 7.53 (m, 3H (1H+2H)), 7.37 (m, 3H), 6.84 (br s, 1H), 6.45 (d, 1H, J=3.4 Hz), 5.21 (s, 2H), 1.54 (s, 9H), 1.45 (s, 9H); IR (neat) $v_{max}$ 3395, 2977, 1759, 1727, 1603, 1577, 1517, 1367, 1346, 1228, 1154, 1111 cm$^{-1}$; FABHRMS (NBA-CsI) m/z 697.0176 (M+Cs$^+$, C$_{25}$H$_{29}$IN$_2$O$_5$ requires 697.0176).

$N^5$-(3-Chloro-2-propen-1-yl)-$N^5$,1-di-((tert-butyloxy)carbonyl)-5-amino-7-(benzyloxy)-4-iodoindole (11d)

Sodium hydride (22 mg, 0.54 mmol, 3 eq, 60% dispersion) was added to a stirred solution of compound (10d) (100 mg, 0.18 mmol) in DMF (5 mL). After 15 min at RT, E/Z-1,3-dichloropropene (0.025 mL, 0.27 mmol) was added. The solution was stirred at Rt for 1 hr. Water (50 mL) and ethyl acetate (50 mL) were then added and the organic layer was separated. The aqueous layer was extracted with ethyl acetate (50 mL) and the combined organic layers were dried (MgSO$_4$) and concentrated. Chromatography (2×15 cm SiO$_2$, ethyl acetate/hexanes 1:9) gave the pure compound (75.4 mg, 66%) as a mixture of E and Z isomers: $^1$H NMR (CDCl$_3$, 400 MHz) major rotamer 7.47 (br s, 1H), 7.36 (m, 5H), 6.53 (m, 1H), 6.00 (m, 2H), 5.17 (s, 2H), 4.51 (m, 1H), 4.11 (m, 1H), 1.54 (s, 9H), 1.25 (s, 9H); IR (neat) $v_{max}$ 2976, 1759, 1701, 1630, 1570, 1367, 1157 cm$^{-1}$; FABHRMS (NBA-CsI) m/z 771.0125 (M+Cs$^+$, C$_{28}$H$_{32}$ClIN$_2$O$_5$ requires 771.0099).

What is claimed is:

1. A compound represented by the following structure:

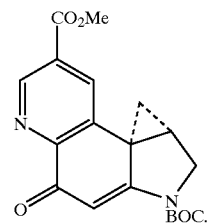

2. A compound represented by the following structure:

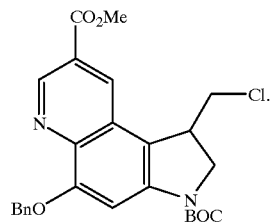

3. A compound represented by the following structure:

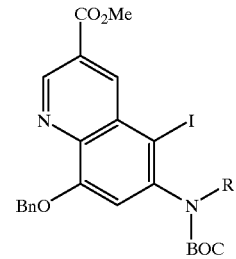

wherein R is a radical selected from the group consisting of H and —CH$_2$CHCHCl.

* * * * *